US012653965B2

(12) United States Patent
Helmer

(10) Patent No.: US 12,653,965 B2
(45) Date of Patent: Jun. 16, 2026

(54) PACKAGING ASSEMBLY

(71) Applicant: Sanofi, Paris (FR)

(72) Inventor: Michael Helmer, Frankfurt am Main (DE)

(73) Assignee: SANOFI, Paris (FR)

( * ) Notice: Subject to any disclaimer, the term of this patent is extended or adjusted under 35 U.S.C. 154(b) by 114 days.

(21) Appl. No.: 18/310,746

(22) Filed: May 2, 2023

(65) Prior Publication Data

US 2023/0364354 A1 Nov. 16, 2023

Related U.S. Application Data

(62) Division of application No. 16/630,066, filed as application No. PCT/EP2018/068502 on Jul. 9, 2018, now Pat. No. 11,672,923.

(30) Foreign Application Priority Data

Jul. 14, 2017 (EP) ..................................... 17305942

(51) Int. Cl.
A61M 5/44 (2006.01)
A61M 5/00 (2006.01)

(52) U.S. Cl.
CPC .............. *A61M 5/44* (2013.01); *A61M 5/002* (2013.01); *A61M 2205/14* (2013.01);
(Continued)

(58) Field of Classification Search
CPC ...... A61M 2205/3368; A61M 2205/14; A61M 2205/18; A61M 2205/3561;
(Continued)

(56) References Cited

U.S. PATENT DOCUMENTS 5,792,117 A 8/1998 Brown
6,482,185 B1 11/2002 Hartmann
(Continued)

FOREIGN PATENT DOCUMENTS

CN 101848742 9/2010
CN 104955435 9/2015
(Continued)

OTHER PUBLICATIONS

International Preliminary Report on Patentability in Application No. PCT/EP2018/068502, dated Jan. 14, 2020, 6 pages.
(Continued)

*Primary Examiner* — Quynh-Nhu H. Vu
(74) *Attorney, Agent, or Firm* — Bond, Schoeneck & King, PLLC

(57) ABSTRACT

A packaging assembly comprises a case configured to contain at least one injection device for delivering a medicament; a cooling unit configured to lower an internal temperature of the case; a processing arrangement; a device sensor configured to detect at least one injection device contained within the case, and to receive device storage information from the at least one detected injection device; and a data storage device. The processing arrangement is configured to record an injection history on the data storage device. The processor arrangement is configured to control the cooling unit to set an internal temperature of the case according to the received device storage information.

13 Claims, 5 Drawing Sheets

(52) U.S. Cl.
CPC . *A61M 2205/18* (2013.01); *A61M 2205/3368* (2013.01); *A61M 2205/3561* (2013.01); *A61M 2205/3606* (2013.01); *A61M 2205/3673* (2013.01); *A61M 2205/50* (2013.01); *A61M 2205/502* (2013.01); *A61M 2205/581* (2013.01); *A61M 2205/584* (2013.01); *A61M 2205/587* (2013.01); *A61M 2205/6054* (2013.01)

(58) Field of Classification Search
CPC .. A61M 2205/3569; A61M 2205/3584; A61M 2205/3606; A61M 2205/36; A61M 2205/3673; A61M 2205/50; A61M 2205/502; A61M 2205/52; A61M 2205/581; A61M 5/002; A61M 5/44; G16H 20/17
See application file for complete search history.

(56) References Cited

U.S. PATENT DOCUMENTS

| | | | |
|---|---|---|---|
| 7,212,955 B2 | 5/2007 | Kirshenbau et al. | |
| 8,172,082 B2* | 5/2012 | Edwards | A61M 5/2033 |
| | | | 604/189 |
| 8,357,114 B2 | 1/2013 | Poutiatine et al. | |
| 9,145,572 B2 | 9/2015 | Nakamura | |
| 9,526,838 B2 | 12/2016 | Baran et al. | |
| 10,773,032 B2* | 9/2020 | Cirillo | G01D 5/34 |
| 2009/0128330 A1 | 5/2009 | Monroe | |
| 2012/0259655 A1 | 10/2012 | Madreperla | |
| 2013/0175192 A1 | 7/2013 | Iio et al. | |
| 2013/0195326 A1* | 8/2013 | Bear | A61J 7/0084 |
| | | | 382/128 |
| 2013/0197445 A1 | 8/2013 | Schabbach et al. | |
| 2015/0251839 A1 | 9/2015 | Denny et al. | |
| 2017/0119954 A1 | 5/2017 | Weinstein et al. | |
| 2017/0216524 A1 | 8/2017 | Haider et al. | |
| 2017/0270276 A1 | 9/2017 | Saint et al. | |
| 2017/0274149 A1 | 9/2017 | Aeschlimann | |
| 2017/0312445 A1* | 11/2017 | Mirov | B29C 65/40 |
| 2020/0164160 A1 | 5/2020 | Helmer | |
| 2020/0289740 A1* | 9/2020 | Tamtoro | A61J 7/0409 |

FOREIGN PATENT DOCUMENTS

| | | |
|---|---|---|
| CN | 106663139 | 5/2017 |
| EP | 3010660 | 4/2016 |
| EP | 3449575 | 3/2019 |
| JP | 2013-521963 | 6/2013 |
| WO | WO 2009/018120 | 2/2009 |
| WO | WO 2010/052470 | 5/2010 |
| WO | WO 2011/117212 | 9/2011 |
| WO | WO 2014/089083 | 6/2014 |
| WO | WO 2014/204958 | 12/2014 |
| WO | WO 2015/187793 | 12/2015 |
| WO | WO 2017/093198 | 6/2017 |
| WO | WO 2017/106247 | 6/2017 |
| WO | WO 2017/186402 | 11/2017 |

OTHER PUBLICATIONS

International Search Report and Written Opinion in Application No. PCT/EP2018/068502, dated Sep. 28, 2018, 9 pages.

* cited by examiner

PACKAGING ASSEMBLY

CROSS-REFERENCE TO RELATED APPLICATIONS

The present application is a divisional application of U.S. patent application Ser. No. 16/630,066, filed on Jan. 10, 2020, which is the national stage entry of International Patent Application No. PCT/EP2018/068502, filed on Jul. 9, 2018, and claims priority to Application No. EP 17305942.9, filed on Jul. 14, 2017, the disclosures of which are incorporated herein by reference.

TECHNICAL FIELD

The application relates to a packaging assembly for a medicament and, in particular, although not exclusively, to a packaging assembly configured to keep the medicament at a suitable temperature, and to record an injection history of the medicament.

BACKGROUND

Patients suffering chronic disease require regular treatment with medicaments, e.g. on the basis of a predefined schedule. Particular medicaments require refrigerated storage, and are often stored refrigerated in a household refrigerator or fridge. In a home treatment environment, the patient stores the medicament in their fridge and administers a predefined dose as required. Hence, the medicament is typically provided in a secondary packaging for convenient placement and storage in the household fridge. However, the user may travel for a number of days or weeks. During travelling, the medicament storage can be a problem.

Depending on the dosage form of the medicament, the secondary packaging containing the medicament may store a primary packed medicament itself, or may store one or more different kinds of drug delivery devices. For instance, the medicament may be provided in a pre-filled syringe or pen-type injector.

A medicament may have a predefined dosing schedule which requires the administration of a dose at relatively long intervals, for instance every two or four weeks, or once a month. The medicament may be provided in a secondary packaging containing several doses which may be stored for 1 to 6 months for instance. It can be difficult for patients to keep track of each scheduled dosing time, particularly when travelling. It can also be difficult for a patient to correctly administer a medicament.

SUMMARY

According to an embodiment, a packaging assembly is provided according to the claims.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying figures, in which.

DETAILED DESCRIPTION

Figure 1:
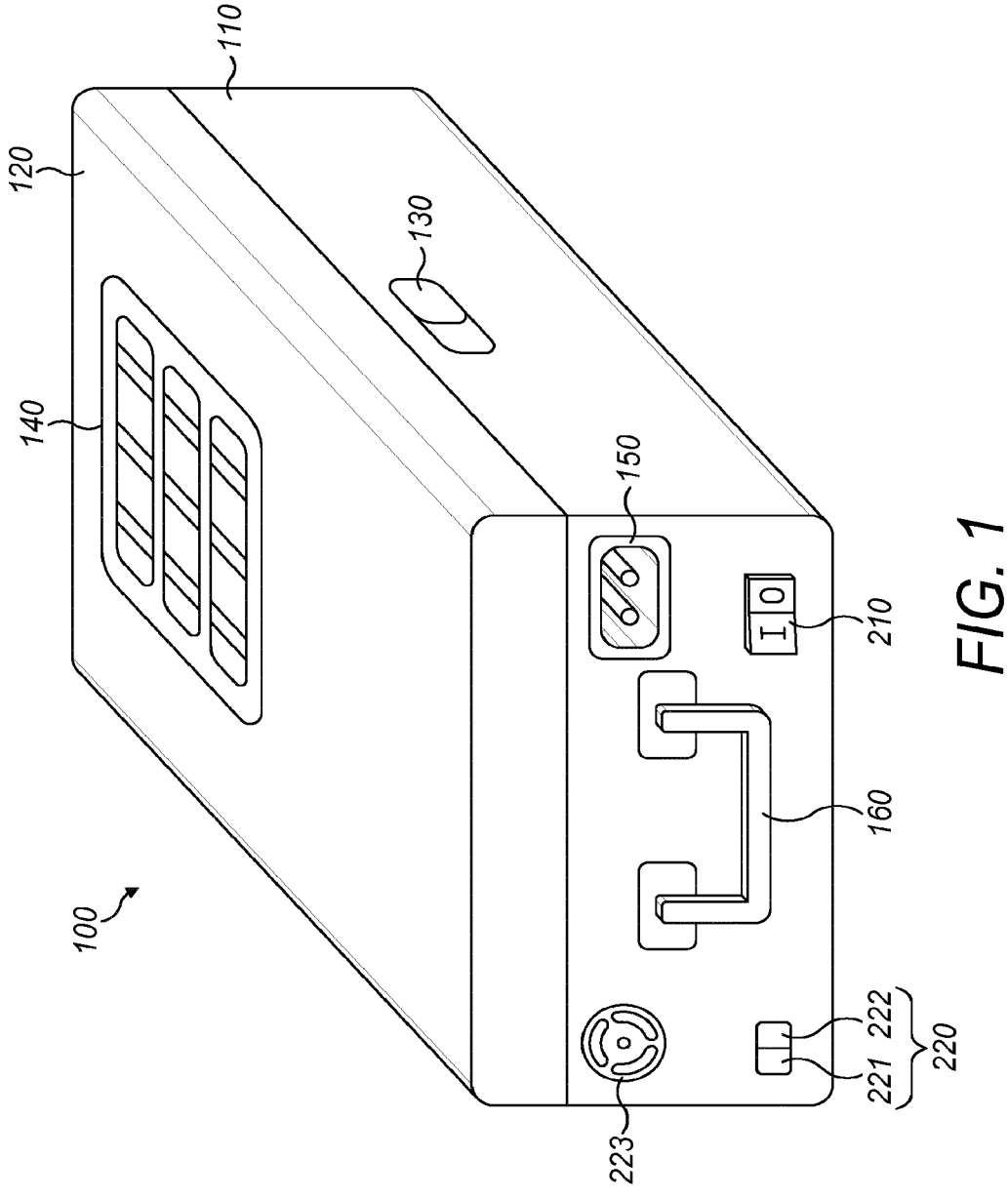
FIG. 1 is an isometric view of a packaging assembly according to a first exemplary embodiment.

Embodiments of the disclosure provide a packaging assembly configured to contain and store a plurality of injection devices for delivering a medicament. An injection device is an example of a drug delivery device and may be a pen-injector or an auto-injector. The packaging assembly is configured to detect the injection devices stored therein, and may be configured to contain a plurality of types of injection device. The packaging assembly is configured to lower the temperature of the injection devices stored therein. The packaging assembly is further configured to store an injection history of the injection device.

The packaging assembly provides an improved arrangement for a user to travel with a plurality of injection devices. The packaging assembly allows the user to travel with the injection devices stored at a suitable temperature. The packaging assembly further provides an injection history for the injection devices used while the user is travelling. Embodiments may further provide reminder notification for using the injection devices, and operating instructions for the injection devices. The packaging assembly provides a compact storage and aide for improving the convenience of a user while travelling.

A drug delivery device, as described herein, may be configured to inject a medicament into a patient. For example, delivery could be sub-cutaneous, intra-muscular, or intravenous. Such an injection device could be operated by a patient or care-giver, such as a nurse or physician, and can include various types of safety syringe, pen-injector, or auto-injector. The injection device can include a cartridge-based system that requires piercing a sealed ampule before use. Volumes of medicament delivered with these various injection devices can range from about 0.2 ml to about 3 ml. Yet another injection device can be represented by a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described injection devices may also be customized to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, an injection device will often include a hollow needle ranging from about 25 to about 31 Gauge in size. Common sizes are 27 and 29 Gauge.

The injection devices described herein can also include one or more automated functions. For example, one or more of needle insertion, medicament injection, and needle retraction can be automated. Energy for one or more automation steps can be provided by one or more energy sources.

Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanisms to cause the automated function. For example, a user may depress a needle sleeve against their body to cause injection of a medicament. In other devices, a user may be required to depress a button and retract a needle shield to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

With reference to FIG. 1, a packaging assembly 100 according to exemplary embodiments is shown. The packaging assembly 100 comprises a case 110 having a lid 120. The lid 120 is attached to the case 110 in a hinged manner. The lid 120 can be freely moved in a hinged manner between a closed position and an open position. In the closed position, the lid 120 is arranged to cover an opening of the case 110. In the open position, the opening of the case 110 is uncovered and an interior of the case 110 can be accessed.

The case 110 is configured to hold and store a plurality of injection devices 10. A length of the case 110 is sufficient to accommodate the length of each of the injection devices 10. The length of the case may be approximately 250 mm. A depth of the case 110, measured between the top of the lid 120 and the base of the case 110, may be approximately 150 mm. A width of the case 110 is sufficient to accommodate four injection devices 10. The width of the case may be approximately 200 mm.

The lid 120 may comprise a latching mechanism 130 to hold the lid 120 in the closed position. The latching mechanism 130 may comprise a sliding catch arranged to slidably move between a first position and a second position. In the first position, the latching mechanism 130 is in a locked state and holds the lid 120 in the closed position. In the second position, the latching mechanism 130 is in an unlocked state and allows the lid 120 to be moved from the closed position to the open position. The latching mechanism 130 may comprise biasing means to urge the catch to the first position.

The packaging assembly 100 comprises a cooling unit 140. The cooling unit 140 is positioned in the lid 120. Alternatively, the cooling unit 140 may be positioned in a side wall or the base of the case 110. The cooling unit 140 is configured to cool the interior of the packaging assembly 100.

The cooling unit 140 is a thermoelectric cooling device e.g. a Peltier device. The cooling unit 140 is a solid-state device which, upon the application of a DC voltage, is configured to move heat from one side of the device to another side of the device. The cooling unit 140 is arranged in the lid 120 such that heat is moved from a side of the device which faces the interior of the packaging assembly 100 to a side of the device which faces an exterior of the packaging assembly 100. Alternatively, the cooling unit 140 may operate to cool the interior of the packaging assembly 100 using a vapor-compression refrigeration process.

Figure 4:
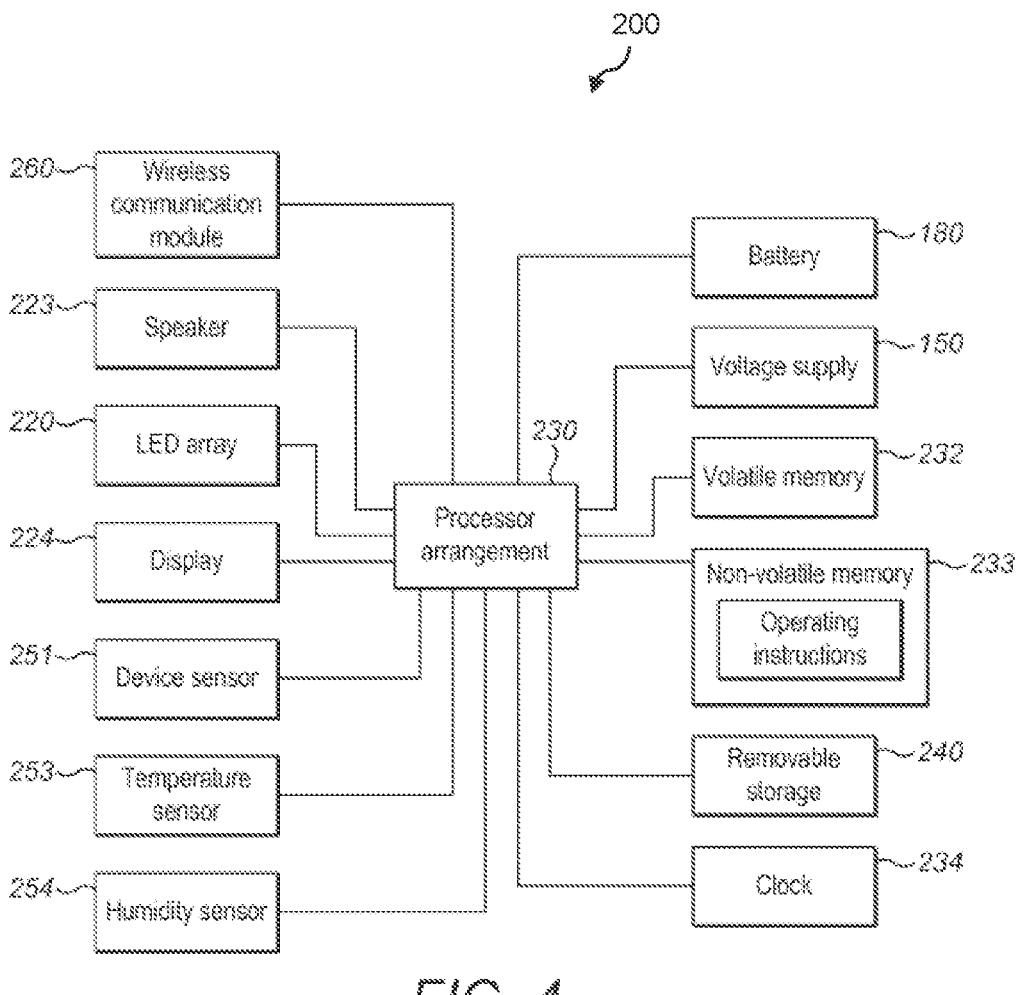
FIG. 4 is a system diagram of the packaging assembly of FIG. 1 in an exemplary operating environment.

The packaging assembly 100 includes an electronics system 200 (shown schematically in FIG. 4). The electronics system 200 comprises multiple components that are connected together to provide a specific set of functions, described below. The components of the electronics system 200 may be mounted on a printed circuit board, or instead they may be interconnected through some other medium.

The electronics system 200 comprises a power switch 210. The power switch 210 is a manual switch moveable between a first position and second position. The power switch 210 may be a rocker switch, a sliding switch or a push button switch. The power switch 210 is arranged on a side wall of the case 110. The power switch 210 is configured to control the supply of power to the electronics system 200 and the cooling unit 140. In the first position, the power switch 210 is in an "off" position, and no power is supplied to the electronics system 200 and the cooling unit 140. In the second position, the power switch 210 is in an "on" position, and power is supplied to the electronics system 200 and the cooling unit 140.

The electronics system 200 comprises a light-emitting diode (LED) array 220. The LED array 220 is an example of an optical transducer. The LED array 220 comprises an array of two light-emitting diodes (LEDs). The LEDs of the LED array 220 are arranged on a side wall of the case 110. Each of the LEDs can be illuminated with a different color. For example, the LED array 220 may comprise a green LED 221 and a red LED 222. Alternatively, the LED array 220 may comprise a single two-color LED. The LED array 220 is configured to output a temperature status of the packaging assembly 100.

The electronics system 200 comprises a speaker 223. The speaker 223 is an example of an audio transducer. The speaker 223 is arranged on a side wall of the case 110. The speaker 223 is configured to provide the user with an audio reminder when the scheduled dosing time for an injection device 10 is due.

The packaging assembly 100 comprises a voltage supply 150. The voltage supply 150 is configured to supply DC power to the electronics system 200 and the cooling unit 140. The voltage supply 150 is arranged to receive power from an external power supply. The voltage supply 150 may comprise a transformer to convert AC power received from an external power supply or to convert DC power received at a different voltage level.

The packaging assembly 100 comprises a handle 160. The handle 160 is a loop handle arranged to be grasped by a user, to carry the packaging assembly 100. The handle 160 is attached to a side wall of the case 110 with a hinge attachment. Alternatively, the handle 160 may be attached to the lid 120. Further alternatively, the handle 160 may be attached with a fixed attachment, or may be formed as an integral part of the case 110 or the lid 120.

Figure 2:
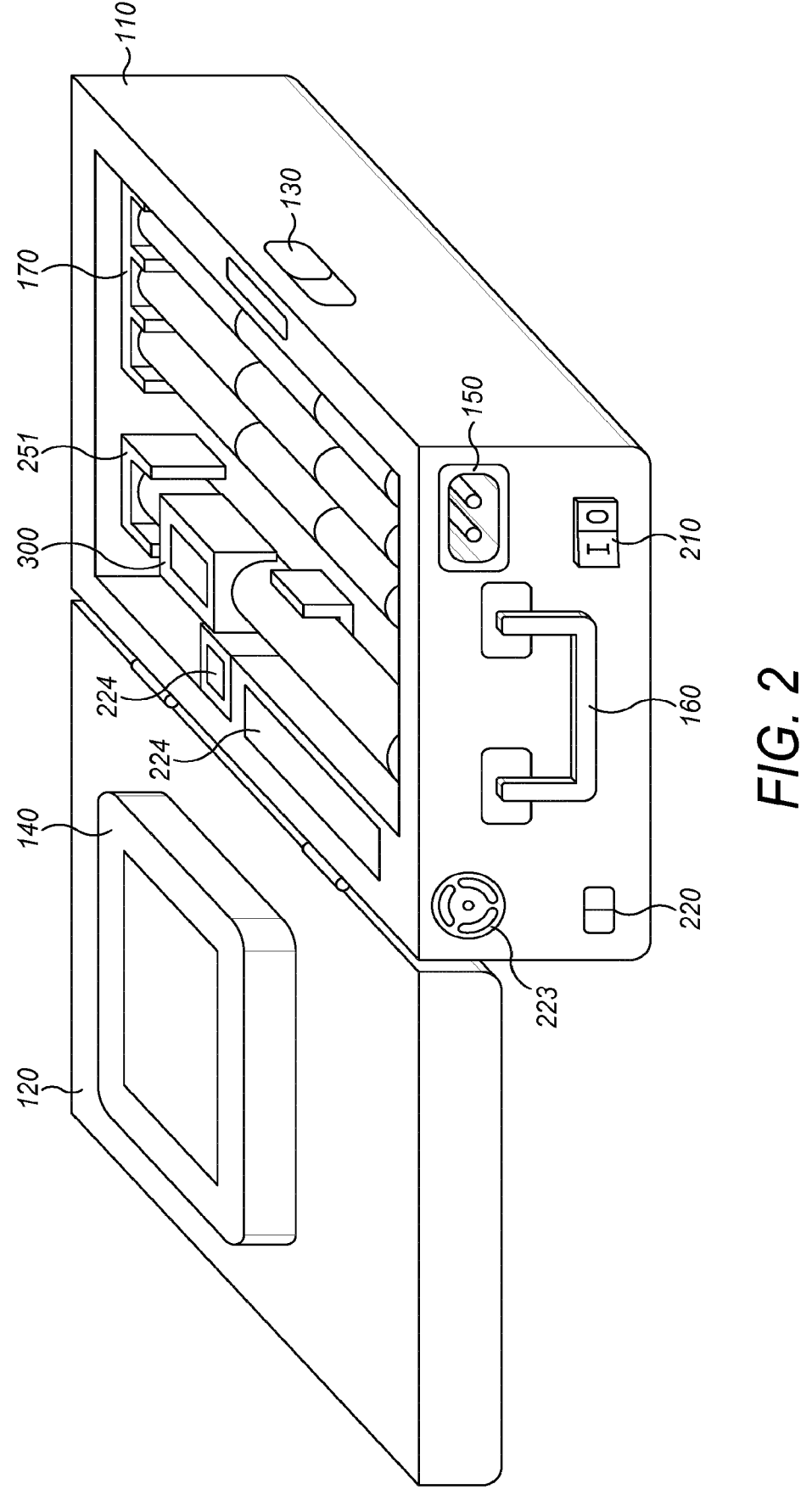
FIG. 2 is an isometric view of the packaging assembly of FIG. 1.

FIG. 2 shows the packaging assembly 100 from the front with the lid 120 in the open position.

The latching mechanism 130 can be seen in more detail. The latching mechanism 130 comprises a sliding catch arranged to protrude from a side wall of the case 110. The protruding part of the sliding catch is configured to engage with a corresponding feature in the lid 120 when the lid 120 is in the closed position. The latching mechanism may comprise biasing means, e.g. a spring, to urge the sliding catch to the first position. The sliding catch may be configured to engage with an opening in the lid 120 in the first position when the lid is in the closed position. The sliding catch may engage with the opening to maintain the lid 120 in the closed position.

Alternately, the lid 120 may comprise a protruding part which is disposed in a corresponding slot in the side wall of the case 110 when the lid 120 is in the closed position, and the sliding catch may be configured to engage with the protruding part of the lid 120.

Alternatively, the latching mechanism 130 may be a sprung push-catch push-release mechanism. The latching mechanism 130 may be configured to engage with a first push into the closed position and maintain the lid 120 in the closed position. The latching mechanism 130 may be configured to disengage with a second push and allow the lid 120 to open. The latching mechanism 130 may be configured to engage whenever the lid 120 is closed to hold the lid 120 in the closed position. The latching mechanism 130 may further comprise a release switch to disengage the latching mechanism 130 and allow the lid 120 to open. The release switch may be a mechanical switch or an electric switch. The release switch may be an electric switch coupled to a code input, which is configured to disengage the latching mechanism 130 when a correct code is entered.

The latching mechanism 130 is arranged on a side wall of the case 110 which is opposite the hinged attachment of the lid 120.

The packaging assembly 100 as shown contains a plurality of injection devices 10, each of which may be of a different device type, and will be discussed in more detail later with reference to FIGS. 5A and 5B. Different types of injection device 10 may provide different medicaments. Alternatively, different types of injection device 10 may have different dosages or concentrations of the same medicament, or different methods of delivering the medicament. Different types of injection device 10 may have different dosing intervals.

For example, a dosing time for one type of injection device 10 may be scheduled every 14 days or 28 days, according to the prescription and/or product patient leaflet of the medicament provided with the injection device 10. For some injection devices 10, a period of time between scheduled dosing times may be between 2 days and 60 days, according to the requirements of the medicament. The packaging assembly 100 may be configured to contain and store injection devices 10 of multiple types, simultaneously or at different points in time. The packaging assembly 100 may contain a plurality of injection devices 10 providing one or more different medicaments with one or more different dosing intervals.

The packaging assembly 100 may be configured to hold more than four, or fewer than four injection devices 10 in the case 110. The injection devices 10 are arranged within the case 110 with the next injection device 10 to be used separated from the remaining "reservoir" of injection devices 10. As shown in FIG. 2, one injection device 10 is separated from the remaining three injections devices 10.

The injection devices 10 may be retained in position within the case 110 in a corresponding plurality of slots 170.

Each injection device 10 may be retained in a corresponding slot 170 by a friction fit with the edges of the slot 170. A retention mechanism may retain the plurality of injection devices 10 in position within the slots 170. The retention mechanism may comprise a pair of springs, e.g. coil springs or flat springs, located at opposite ends of each slot 170. Alternatively, a mechanical catch may be configured to engage with each injection device 10, for example, a sprung lever at each end of the slot 170. A release button or switch may be provided for each slot 170, which is configured to eject the injection device 10 when pressed.

The lid 120 may be configured to retain the plurality of injection devices 10 in position within the case 110 when in the closed position. The lid 120 may be arranged in the closed position to prevent the injection devices 10 from falling or sliding out of the case 110.

A user may receive the packaging assembly 100 in an empty condition. When the user is supplied with a plurality of injection devices 10 they can be loaded into the packaging assembly 100. The lid 120 is moved into the open position and each of the injection devices 10 is inserted into a slot 170. The lid 120 is moved into the closed position. The power switch 210 is moved to the on position to activate the cooling unit 140 and lower the temperature in the case 110. Alternatively, the packaging assembly 100 may be placed in a refrigerator to lower the internal temperature of the case. Further alternatively, the temperature of the packaging assembly 100 may be lowered, using the cooling unit 140 or a refrigerator, prior to the insertion of the injection devices 10.

The electronics system 200 comprises a temperature sensor 253 (shown schematically in FIG. 4), such as a thermistor or thermocouple. The temperature sensor 253 may be fixed in any position inside the case 110. The temperature sensor 253 is configured to output a signal indicating the temperature in the interior of the case 110.

The electronics system 200 may further comprise a humidity sensor 254 (shown schematically in FIG. 4), such as a humistor or a capacitive hygrometer. The humidity sensor 254 may be fixed in any position inside the case 110. The humidity sensor 254 is configured to output a signal indicating the humidity in the interior of the case 110.

The LED array 220 is configured to indicate a status of the temperature within the case 110. The output of the LED array 220 is controlled based on the signal output by the temperature sensor 253. If the temperature detected by the temperature sensor 253 is higher than a threshold temperature, the red LED 222 may be illuminated. If the temperature detected by the temperature sensor 253 is lower than the threshold temperature, the green LED 221 may be illuminated. The temperature threshold is set according to the required storage conditions of the injection devices 10.

Alternatively, or in addition, the electronics system 200 may comprise a temperature display. The temperature display may comprise two seven-segment light-emitting diode (LED) arrays, which can be operated to show any number from 00 to 99 by illuminating some or all of the LED segments. The temperature measured by the temperature sensor 253 may be shown on the temperature display in degrees of Celsius or degrees of Fahrenheit.

The electronics system 200 comprises a display 224. The display 224 is positioned in an interior of the case 110. The display 224 is obscured when the lid 120 is in the closed position, and is uncovered when the lid 120 is in the open position. The display 224 is a flat panel display such as an LCD or an OLED panel. The display 224 is configured to output status information of the packaging assembly 100 and the injection devices 10. The display 224 may output the measured temperature and/or humidity within the case 110. The display 224 may output the number and/or type of injection devices 10 contained in the case 110. The display 224 may output the schedule dosage time or expiry date of one or more injection devices 10.

The display 224 is configured to show instructions for the administration of a medicament using one of the injection devices 10. The display 224 is configured to show instructions for the operation of the next injection device 10 to be used. Instructions may be shown in the form of text, diagrams or video instructions. Audio may be provided by the speaker 223. Instructions for the use of each injection device 10 may be stored by the processor arrangement 230 or may be received by the device sensor 251 from the injection device 10. The display 224 may show instructions for the operation of an injection device 10 when the scheduled dosing time is due or, alternatively, when the injection device 10 is removed from the case 110.

The electronics system 200 comprises a processor arrangement 230 (shown schematically in FIG. 4). The processor arrangement 230 controls operation of the other hardware components of the electronics system 200. The processor arrangement 230 is configured to control the hardware components which form the user interface 210. The processor arrangement 230 is configured to process one or more input signals from at least one input sensor.

The electronics system 200 comprises a removable storage 240. The removable storage 240 is an example of a data storage device. The removable storage 240 is a solid state storage medium e.g. an SD card or microSD card. The processor arrangement 230 is configured to write data to the removable storage 240 and read data from the removable storage 240.

The processor arrangement 230 is configured to record status information of the packaging assembly 100 on the removable storage 240. The processor arrangement 230 records a plurality of temperature measurements output by the temperature sensor 253 onto the removable storage 240. The processor arrangement 230 records a plurality of humidity measurements output by the humidity sensor 254 onto the removable storage 240. The processor arrangement 230 records the status information of the packaging assembly 100 at a regular predetermined interval, for example, once every day, once every hour or once every ten minutes.

The processor arrangement 230 records status information for one or more injection devices 10 stored in the packaging assembly 100 on the removable storage 240. The processor arrangement 230 may record the number and/or type of injection devices 10 contained in the case 110 on the removable storage 240. The processor arrangement 230 may record the schedule dosage time or expiry date of one or more injection devices 10 on the removable storage 240. The processor arrangement 230 records an injection history on the removable storage 240 comprising information on each injection carried out by the user.

The electronics system 200 comprises a device sensor 251. The device sensor 251 is arranged in proximity to the slot 170 holding the next injection device 10 to be used. The device sensor 251 is a radio-frequency identification (RFID) reader comprising a radio-frequency antenna.

The device sensor 251 is arranged to detect a device tag located on the injection device 10. The device tag is a passive RFID tag comprising a radio-frequency antenna. The device sensor 251 generates an electromagnetic field, which activates the device tag, and detects a response signal transmitted by the device tag. The device sensor 251 may be configured to read device information stored on the device tag.

The device sensor 251 may include electronic components that are separate to the device sensor 251 but form part of the device sensor 251 itself. The device sensor 251 may provide signals transmitted by a device tag and the electronic components perform analysis of the signal and communication to the processor arrangement 230. Alternatively, the device sensor 251 may include electronic components to perform analysis of a detected signal. Further alternatively, the analysis of incoming signals may be performed by the processor arrangement 230.

The electronics system 200 further comprises a wireless communication module 260 (shown schematically in FIG. 4). The wireless communication module 260 is configured to communicate wirelessly with one or more devices external to the packaging assembly 100, under the control of the processor arrangement 230. The wireless communication module 260 may be configured to establish communication using a short range communication protocol such as Bluetooth, ZigBee, Infrared Data Association (IrDA) or similar, using a wireless local area network (LAN) such as a Wi-Fi or Li-Fi network, or using a mobile communication protocol such as GSM, CDMA, EDGE, GPRS, HSPA, WiMAX, LTE or similar.

The wireless communication module 260 is configured to transmit signals from the processor arrangement 230 to an external user device. The wireless communication module 260 is configured to receive signals transmitted by the external user device. Transmitted signals may be encrypted or otherwise protected to ensure data privacy and data integrity. A pairing process may be required between the wireless communication module 260 and the external user device to establish an authorized wireless communication.

The external user device may be e.g. a personal computer or a mobile phone. The external user device can be operated by, for example, a caregiver or a parent/guardian of the patient. The external user device may be located in proximity to the packaging assembly 100, or at a remote location from the packaging assembly 100. For example, the external user device may be located at a place of work or residence of the caregiver which is remote from the residence of the patient. In this case, the wireless communication module 260 may connect with the external user device through the internet, via a wireless access point such as a wireless router.

The processor arrangement 230 is configured to transmit the contents of the removable storage 240 to the external user device. The processor arrangement 230 is configured to transmit the injection history recorded on the removable storage 240. The processor arrangement 230 is configured to transmit the status information of the packaging assembly 100 and/or the one or more injection devices 10 recorded on the removable storage 240. The processor arrangement 230 may be configured to remove data from the removable storage 240 after the data has been transmitted to the external user device.

The processor arrangement 230 may further control the wireless communication module 260 to transmit information relating to the plurality of injection devices 10 to the external user device. The wireless communication module 260 may transmit a current status of the injection devices 10, for example, the wireless communication module 260 may transmit an alert if a scheduled dosing time is due, or may transmit the time remaining until the next scheduled dosing time is due. The wireless communication module 260 may transmit device information received from the device sensor 251, for example, the wireless communication module 260 may transmit the number and type of injection devices 10 stored in the packaging assembly 100. The wireless communication module 260 may transmit an alert to the external user device if one of the injection devices 10 has expired.

The wireless communication module 260 may transmit injection information to the external user device if a scheduled dosing time is due. For example, the wireless communication module 260 may transmit a warm-up time period to the external user device, representing the recommended period of time to wait before injection to allow the injection device 10 to reach room temperature. In this way, the lid 120 may be closed and the external user device may be used to monitor the warm-up time period. The warm-up time period may be fixed or may depend on the type of injection device 10. The warm-up time period for an injection device 10 may be stored by the processing arrangement 230 or may be received by the device sensor 251 from the injection device 10.

Injection information transmitted by the wireless communication module 260 to the external user device may include instructions for the use of the injection device 10. Instructions may be transmitted in the form of text, diagrams or audio or video instructions. Instructions for the use of each injection device 10 may be stored by the processor arrangement 230 or may be received by the device sensor 251 from the injection device 10. Alternatively, the wireless communication module 260 may transmit the ID or the device type of the injection device 10 to the external user device, and the external user device may retrieve the instructions for injection from an external database e.g. via the internet.

The wireless communication module 260 may transmit current status information of the packaging assembly 100 to the external user device. For example, the wireless communication module 260 may transmit current environmental information provided by the temperature sensor 253 or the humidity sensor 254. Alternatively, the wireless communication module 260 may transmit a status alert to the external user device when the status of the packaging assembly 100 is abnormal, for example, when the detected temperature or humidity is too high.

The packaging assembly 100 comprises a plurality of batteries 180 (shown schematically in FIG. 4). The batteries 180 are arranged to provide power to the components of the electronic system 200 and the cooling unit 140. The batteries 180 are configured to receive power from the voltage supply 150 when an external power supply is connected. When the voltage supply 150 is not connected to an external power supply, the electronics system 200 and cooling unit 140 are powered using the plurality of batteries 180.

The packaging assembly 100 further comprises an add-on device 300. The add-on device is an example of a monitoring device. The add-on device 300 is removable from the case 110 and can be attached to one of the injection devices 10. The add-on device 300 is configured to be attached to the next injection device 10 to be used. The slot 170 for the next injection device 10 to be used is configured to accommodate the add-on device 300.

Figure 3:
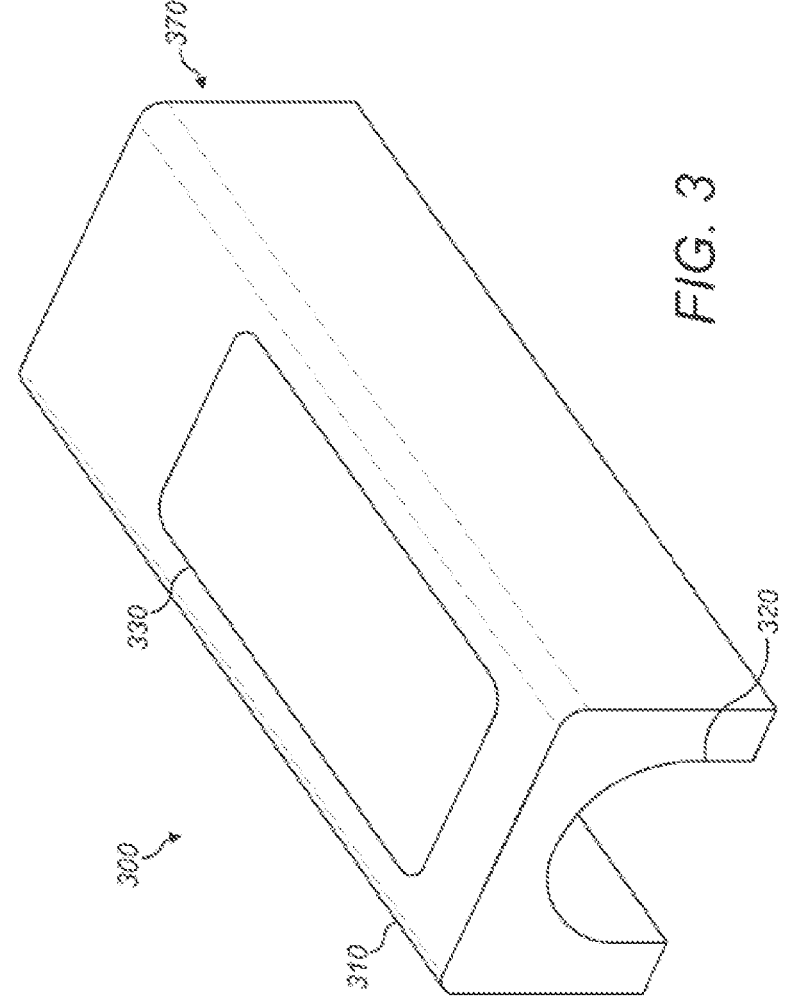
FIG. 3 is an isometric view of an add-on device of the packaging assembly of FIG. 1.

FIG. 3 shows the add-on device 300 in more detail. The add-on device 300 comprises a housing 310, an opening 320, a display 330, a communication unit 340, a device status monitor, a battery, and a docking connector 370.

The add-on device 300 is configured to be attached to an injection device 10. The injection device 10 is received in the opening 320. The add-on device 300 can be attached to the next injection device 10 to be used and placed in the slot 170 with the injection device 10.

The docking connector 370 is configured to connect to a corresponding connector (not shown) in the slot 170 when the add-on device 300 is in position. The battery is charged using power supplied from the batteries 180 or the voltage supply 150 when the docking connector 370 is connected. Alternatively, the add-on device 300 may be charged wirelessly without a docking connector 370. When the add-on device 300 is removed from the case 110, power is supplied to the display 330, communication module 340 and device status monitor by the battery.

The display 330 is a flat panel display such as an LCD or an OLED panel. The display 330 may be a low-power monochrome LCD. Alternatively, the display 330 may be a transreflective or 'e-ink' screen.

The display 330 is configured to show instructions for the administration of a medicament using the injection device 10 to which the add-on device 300 is attached. Instructions may be shown in the form of text, diagrams or audio or video instructions. The display 330 may show instructions for the operation of an injection device 10 when the injection device 10 is removed from the case 110. The display 330 may further show a warm-up time period, representing the recommended period of time to wait before injection to allow the injection device 10 to reach room temperature.

The wireless communication module 260 is configured to communicate wirelessly with the communication module 340 of the add-on device 300. The wireless communication module 260 may be configured to establish communication using a short range communication protocol such as Bluetooth, ZigBee, Infra-red Data Association (IrDA) or similar. The wireless communication module 260 is configured to transmit signals from the processor arrangement 230 to the add-on device. The wireless communication module 260 is configured to receive signals transmitted by the communication unit 340. Transmitted signals may be encrypted or otherwise protected to ensure data privacy and data integrity. A pairing process may be required between the wireless communication module 260 and the add-on device 300 to establish an authorized wireless communication.

The wireless communication module 260 may transmit injection information to the add-on device 300. For example, the wireless communication module 260 may transmit the warm-up time period to the add-on device 300. Injection information transmitted by the wireless communication module 260 to the add-on device 300 may include instructions for the use of the injection device 10. Instructions may be transmitted in the form of text, diagrams or audio or video instructions. Instructions for the use of each injection device 10 may be stored by the processor arrangement 230 or may be received by the device sensor 251 from the injection device 10.

The device status monitor is located within the opening 320. The device status monitor is configured to detect an injection status of the injection device 10. The device status monitor may comprise a mechanical switch, which is arranged to be depressed by a needle shield of the injection device 10 when the injection is complete. Alternatively, the device status monitor may be an optical sensor arranged to detect a change in the color of a status indicator on the injection device 10 when the injection is complete. Alternatively, the device status monitor may be an RFID sensor configured to receive an RFID signal output by the injection device 10 when the injection is complete.

The communication unit 340 is configured to transmit the detected injection status to the wireless communication module 260. The processing arrangement 230 is configured to record the received injection status on the removable storage 240. The injection history recorded by the processing arrangement 230 on the removable storage 240 comprises the injection status of each injection device 10 which is operated by the user.

The electronics system 200 is shown schematically in FIG. 4.

With respect to FIG. 4, a schematic representation of the electronics system 200 of the packaging assembly 100 is shown. The electronics system 200 comprises the processor arrangement 230. The processor arrangement 230 and other hardware components may be connected via a system bus (not shown). Each hardware component may be connected to the system bus either directly or via an interface. One or more batteries 180 are arranged to provide power to the electronics system 200.

The processor arrangement 230 controls operation of the other hardware components of the electronics system 200. The processor arrangement 230 may be an integrated circuit of any kind. The processor arrangement 230 may for instance be a general purpose processor. It may be a single core device or a multiple core device. The processor arrangement 230 may be a central processing unit (CPU) or a graphics processing unit (GPU). Alternatively, it may be a more specialist unit, for instance a RISC processor or programmable hardware with embedded firmware. Multiple processors may be included. The processor arrangement 230 may be termed processing means.

The processor arrangement 230 has an internal processing clock speed of about 4 MHz. The processor arrangement 230 also has a stand-by clock speed of 2 Hz to reduce energy consumption. The internal processing clock speed and stand-by clock speed are selected to provide a balance between power usage and usability. A greater clock speed provides improved usability by reducing the time required for the processor arrangement 230 to respond to an input. However, a greater clock speed will increase the power usage of the processor arrangement 230. The stand by clock speed may be selected between 0.5 and 100 Hz.

The electronics system 200 comprises a working or volatile memory 232. The processor arrangement 230 may access the volatile memory 232 to process data and may control the storage of data in memory. The volatile memory 232 may be a RAM of any type, for example Static RAM (SRAM), Dynamic RAM (DRAM), or it may be Flash memory. Multiple volatile memories may be included, but are omitted from the Figure.

The electronics system 200 comprises a non-volatile memory 233. The non-volatile memory 233 stores a set of operation instructions for controlling the normal operation of the processor arrangement 230. The non-volatile memory 233 may be a memory of any kind such as a Read Only Memory (ROM), a Flash memory or a magnetic drive memory. Other non-volatile memories may be included, but are omitted from the Figure.

The processor arrangement 230 operates under the control of the operating instructions. The operating instructions may comprise code (i.e. drivers) relating to the hardware components of the electronics system 200, as well as code relating to the basic operation of the packaging assembly 100. The operating instructions may also cause activation of one or more software modules stored in the non-volatile memory 233. Generally speaking, the processor arrangement 230 executes one or more instructions of the operating instructions, which are stored permanently or semi-permanently in the non-volatile memory 233, using the volatile memory 232 temporarily to store data generated during execution of the operating instructions.

The processor arrangement 230, the volatile memory 232 and the non-volatile memory 233 may be provided as separate integrated circuit chips connected by an off-chip bus, or they may be provided on a single integrated circuit chip. The processor arrangement 230, the volatile memory 232 and the non-volatile memory 233 may be provided as a microcontroller.

The electronics system 200 comprises the removable storage 240. The electronics system comprises a slot or port into which one or more removable storage 240 items can be inserted, for example, an SD card or microSD card. The removable storage 240 may be utilize any other suitable storage medium.

The electronics system 200 comprises a clock 234. The clock 234 may be a clock crystal, for example, a quartz crystal oscillator. The clock 234 may be a separate component to the processor arrangement 230 which is configured to provide a clock signal to the processor arrangement 230. The processor arrangement 230 may be configured to provide a real time clock based on the signal from the clock 234. Alternatively, the clock 234 may be a clock crystal which is provide on a single integrated circuit chip with the processor arrangement 230.

The processor arrangement 230 is configured to perform at least one countdown operation. The processor arrangement 230 may perform a different countdown operation for each different type of injection device 10 stored in the packaging assembly 100. The processor arrangement 230 monitors the one or more countdown operations to determine the number of days remaining until the next scheduled dosing time. Countdown operations may be set and activated in response to the addition of each injection device 10 to the case 110, as detected by the device sensor 251. Alternatively, the processor arrangement 230 may monitor a countdown for the next injection device 10 to be used only. The processor arrangement 230 records the number of days for each countdown timer to the volatile memory 232 and every 24 hours reduces the recorded number of days by one.

The predetermined time period for each countdown to the next scheduled dosing time may be different for each different type of device. For example, if a time period until the next scheduled dosing time is due is 14 days for a certain type of device, the countdown timer for that type of device is started from 14 days. If a time period until the next scheduled dosing time is due is 28 days for another type of device, the countdown timer for that type of device is started from 28 days.

Every 24 hours, the number of days recorded to the volatile memory 232 is reduced by one. The processor arrangement 230 monitors the lowest active countdown to determine the number of days remaining until the next scheduled dosing time. On the day of the scheduled dosing time, the processor arrangement 230 may control the electronics system 200 to generate an output to indicate that the next scheduled dosing time is due.

The processor arrangement 230 may be configured to provide a current date and time based on the signal from the clock 234. The processor arrangement 230 may monitor the expiry date for each injection device 10 stored in the packaging assembly 100. The processor arrangement 230 may determine that an injection device 10 has expired when the expiry date is in the past. The processor arrangement 230 may control the electronics system 200 to generate an output to indicate that an injection device 10 has expired.

The processor arrangement 230 may be configured to check the state of charge of one or more batteries 180 included in the packaging assembly 100. The state of charge is determined to be low if it is below a threshold (which may be built into the design of the packaging arrangement). The state of charge may be determined by measurement of the voltage provided by the battery 180, by monitoring energy use from a full state of charge, or a combination of these two techniques.

The electronics system 200 comprises the speaker 223. The speaker 223 can be operated to output a notification signal. The speaker 223 can be operated to provide an indication of a status of the packaging assembly 100. The speaker 223 is an example of a status indicator.

The processor arrangement 230 operated the speaker 223 to provide an audio reminder that the next scheduled dosing time is due. On the day of a scheduled dosing time, the speaker 223 is operated to output an audio reminder that the schedule dosage time is due. The speaker 223 may be operated to output an intermittent tone or tone sequence. The periodicity of the intermittent speaker 223 output may be of the order of 0.25 seconds to 2 seconds.

The processor arrangement 230 may operate the speaker 223 to generate the reminder output until an action is taken by the user. The speaker 223 may be deactivated in response to a detected action by the user. For example, the speaker 223 may be deactivated when it is determined, using the device sensor 251, that an injection device 10 has been removed from the case 110.

The electronics system 200 comprises the temperature sensor 253. The temperature sensor 253 may be mounted on a PCB with the processor arrangement 230. Alternatively, the temperature sensor 253 may be fixed in any position inside the case 110 and connected to the processor arrangement 230 by a cable. The temperature sensor 253 may comprise a thermistor configured to pass a current according to the temperature within the packaging assembly 100. The temperature sensor 253 may be configured to provide a signal of one type (e.g. high) when an internal temperature of the packaging assembly 100 exceeds a threshold, and a signal of an opposite type (e.g. low) when the temperature is below the threshold.

Alternatively, the temperature sensor 253 provides a current signal to the processor arrangement 230 according to the internal temperature of the packaging assembly 100. The received signal may be compared to a threshold by the processor arrangement 230. The threshold may be a preset threshold stored in the non-volatile memory 233, or it may be dynamically adjustable having regard to operating conditions. The electronics system 200 comprises the LED array 220. The processor arrangement 230 is configured to operate the LED array to indicate a status of the temperature within the case 110. The output of the LED array 220 is controlled based on the signal output by the temperature sensor 253. If the temperature detected by the temperature sensor 253 is higher than a threshold temperature, the red LED 222 is illuminated. If the temperature detected by the temperature sensor 253 is lower than the threshold temperature, the green LED 221 is illuminated.

The electronics system 200 comprises the humidity sensor 254. The humidity sensor 254 may be mounted on a PCB with the processor arrangement 230. Alternatively, the humidity sensor 254 may be fixed in any position inside or outside the case 110 and connected to the processor arrangement 230 by a cable. The humidity sensor 254 may comprise a humistor configured to pass a current according to the humidity within the packaging assembly 100. The humidity sensor 254 may be configured to provide a signal of one type (e.g. high) when an internal humidity of the packaging assembly 100 exceeds a threshold, and a signal of an opposite type (e.g. low) when the humidity is below the threshold.

Alternatively, the humidity sensor 254 provides a current signal to the processor arrangement 230 according to the internal humidity of the packaging assembly 100. The received signal may be compared to a threshold by the processor arrangement 230. The threshold may be a preset threshold stored in the non-volatile memory 233, or it may be dynamically adjustable having regard to operating conditions.

The electronics system 200 comprises a device sensor 251. The device sensor 251 is arranged to detect one or more injection devices 10 in the packaging assembly 100. The device sensor 251 may configured to detect an injection device 10 in the slot 170 for the next injection device 10 to be used. The device sensor 251 provides a signal to the processor arrangement 230 to indicate the presence of an injection device 10. The processor arrangement 230 may store a device table in the volatile memory 232 which records details of the detected injection device 10.

The device sensor 251 comprises a radio-frequency (RF) antenna. The processor arrangement 230 operates the device sensor 251 to transmit an RF electromagnetic signal through the antenna. When an injection device 10 is located in proximity to the device sensor 251, the electromagnetic signal activates a device tag on the injection device 10. The device tag comprises an RF antenna and a low power circuit. The device tag is powered through induction by the RF signal broadcast by the device sensor 251.

The device sensor 251 may receive device information from the device tag. The device tag may comprise a non-volatile storage with stored device information. The device tag may be configured to transmit the device information with the response signal when activated by the device sensor 251. The device tag may store one or more of a device ID, a device type, an expiry date, a dosing time period and a warm-up time period for the injection device 10. The device sensor 251 may receive the device information transmitted with the response signal from the device tag. The device sensor 251 sends the received device information to the processor arrangement 230.

Each injection device 10 added to the case 110 may be scanned in turn by the device sensor 251. The processor arrangement 230 may store details of all injection devices 10 in the case 110 in the recorded device table. The details of one or more injection devices 10 stored in the case may be recorded in the removable storage 240.

Alternatively, the packaging assembly may comprise a plurality of device sensors 251 in an array. The plurality of device sensors 251 may be arranged in the case 110. The number of device sensors 251 in the case 110 may corresponds to the number of injection devices 10 which can be stored in the packaging assembly 100. The array of device sensors 251 may comprise one device sensor 251 for each of the slots 170.

The device ID of an injection device 10 represents a unique identifier for the injection device 10. Each injection device 10 has a unique device ID recorded on the device tag. The device type is related to the specific treatment provided by the injection device 10. The device type may be defined by any feature which differentiates injection devices 10 for different treatments. For example, the device type may be defined by one or more of the medicament contained in each injection device 10, the volume or concentration of the medicament and the method of administration.

The device ID may be validated by the processor arrangement 230. The processor arrangement 230 may operate the display 224 to output a visual indication if a device ID is not recognized by the processor arrangement 230.

The dosing time period for a type of injection device 10 represents the period of time required between each scheduled dosing time for the device type. The dosing time period for each injection device 10 may be recorded on the device tag and transmitted to the device sensor 251. Alternatively, a dosing time period for one or more types of injection device 10 may be stored in the non-volatile memory 233 of the electronics system 200. The processor arrangement 230 may record the dosing time period for an injection device 10 in the device table based on the device information received from the device sensor 251.

The expiry date of an injection device 10 represents the latest date on which the injection device 10 is considered suitable for use. When the expiry date is in the past the injection device 10 is considered to be expired and should not be used. The processor arrangement 230 may operate the display 224 to output a visual indication when the expiry date of an injection device 10 is in the past.

Alternatively, the processor arrangement 230 may compare the expiry date of an injection device 10 with the scheduled dosing time for the injection device 10. The processor arrangement 230 may pre-emptively operate the display 224 to output a visual indication when the expiry date of the injection device 10 will pass before the next scheduled dosing time becomes due. The processor arrangement 230 may be further configured to output a warning if the injection device 10 is not suitable for use for any other reason. For example, if the internal temperature of the packaging assembly 100 is recorded as being too high for a predefined period of time, one or more of injection devices 10 stored therein may be treated as having expired.

The processor arrangement 230 may check the state of charge of one or more batteries 180 included in the packaging assembly 100. If the state of charge is determined to be low, the display 224 may be operated to show a battery low warning.

Figures 5A, 5B:
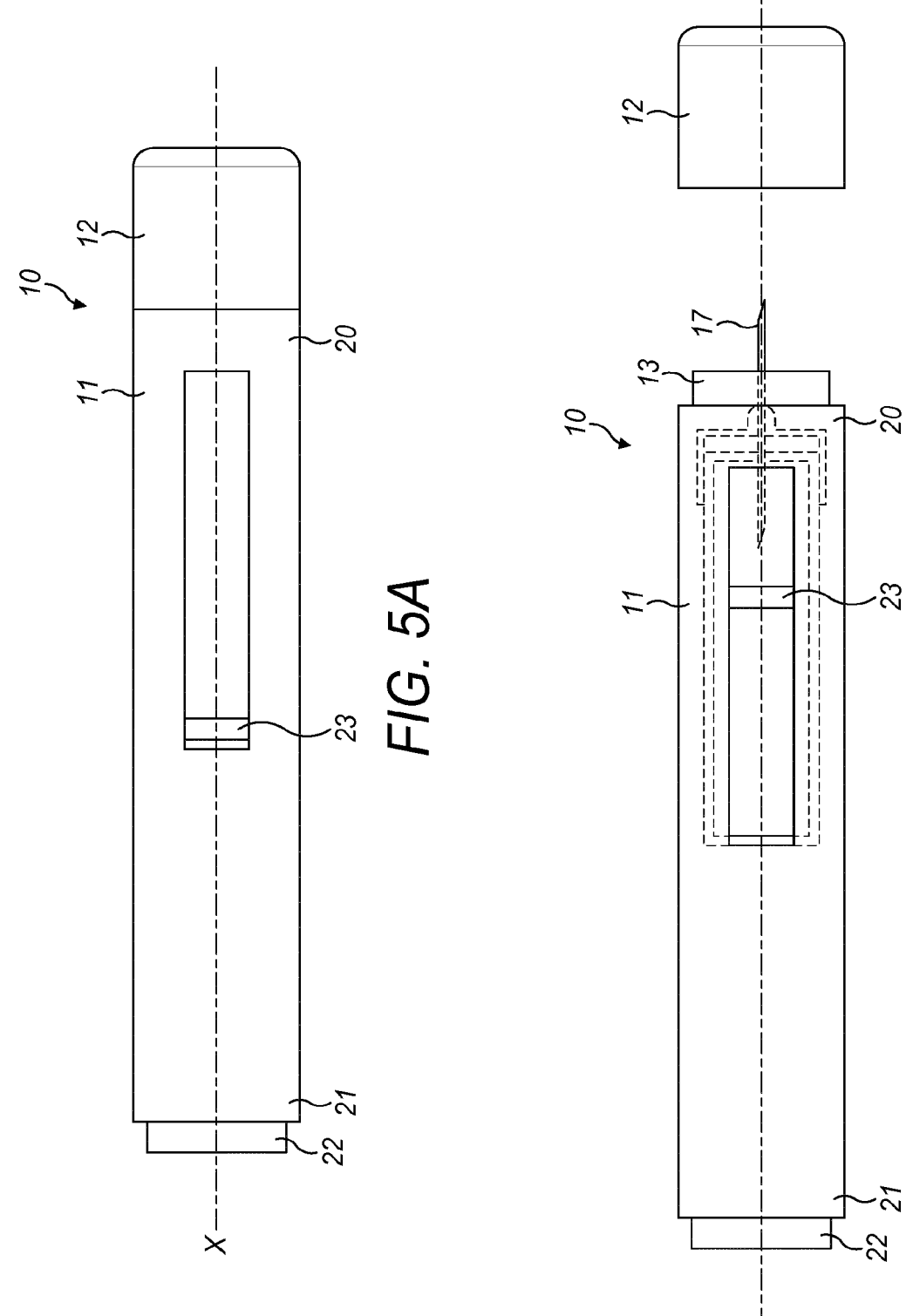
FIGS. 5A and 5B are side-on views of an auto-injection device for use with the packaging assembly, according to an exemplary embodiment.

With respect to FIGS. 5A and 5B, an exemplary injection device 10 is shown. Injection device 10, as described above, is configured to inject a medicament into a user's body. Injection device 10 includes a housing 11 which typically contains a reservoir containing the medicament to be injected (e.g., a syringe) and the components required to facilitate one or more steps of the delivery process. Injection device 10 can also include a cap assembly 12 that can be detachably mounted to the housing 11. Typically a user must remove cap 12 from housing 11 before injection device 10 can be operated.

As shown, housing 11 is substantially cylindrical and has a substantially constant diameter along the longitudinal axis X. The housing 11 has a proximal region 20 and a distal region 21.

The term "proximal" refers to a location that is relatively closer to a site of injection, and the term "distal" refers to a location that is relatively further away from the injection site.

Injection device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a distal direction can permit a needle 17 to extend from proximal region 20 of housing 11.

Insertion of needle 17 can occur via several mechanisms. For example, needle 17 may be fixedly located relative to housing 11 and initially be located within an extended needle sleeve 13. Distal movement of sleeve 13 by placing a proximal end of sleeve 13 against a user's body and moving housing 11 in a proximal direction will uncover the proximal end of needle 17. Such relative movement allows the proximal end of needle 17 to extend into the user's body. Such insertion is termed "manual" insertion as needle 17 is manually inserted via the user's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 4A and 4B, button 22 is located at a distal end of housing 11. However, in other embodiments, button 22 could be located on a side of housing 11.

Other manual or automated features can include drug injection or needle retraction, or both. Injection is the process by which a bung or piston 23 is moved from a distal location within a syringe (not shown) to a more proximal location within the syringe to force a medicament from the syringe through needle 17. In some embodiments, a drive spring (not shown) is under compression before device 10 is activated. A distal end of the drive spring can be fixed within distal region 21 of housing 11, and a proximal end of the drive spring can be configured to apply a compressive force to a distal surface of piston 23. Following activation, at least part of the energy stored in the drive spring can be applied to the distal surface of piston 23. This compressive force can act on piston 23 to move it in a proximal direction. Such proximal movement acts to compress the liquid medicament within the syringe, forcing it out of needle 17.

Following injection, needle 17 can be retracted within sleeve 13 or housing 11. Retraction can occur when sleeve 13 moves proximally as a user removes device 10 from a user's body. This can occur as needle 17 remains fixedly located relative to housing 11. Once a proximal end of sleeve 13 has moved pasta proximal end of needle 17, and needle 17 is covered, sleeve 13 can be locked. Such locking can include locking any distal movement of sleeve 13 relative to housing 11.

Another form of needle retraction can occur if needle 17 is moved relative to housing 11. Such movement can occur if the syringe within housing 11 is moved in a distal direction relative to housing 11. This distal movement can be achieved by using a retraction spring (not shown), located in proximal region 20. A compressed retraction spring, when activated, can supply sufficient force to the syringe to move it in a distal direction. Following sufficient retraction, any relative movement between needle 17 and housing 11 can be locked with a locking mechanism. In addition, button 22 or other components of device 10 can be locked as required.

Injection device 10 comprises a device tag, for example, a passive RFID tag. The device tag may internally or externally mounted on the housing 11. The device tag is configured to activate when placed in an electromagnetic field, and to output a response signal when activated.

The response signal of the device tag may include information related to the injection device 10. Information may be stored on the device tag and transmitted as part of the response signal when the device tag is activated. The device tag may store one or more of a device ID, device type, expiry date, dosing time period and warm-up time period of the injection device 10.

The packaging assembly 100 may contain or store a plurality of different types of injection device 10 with different information stored on each device tag. Each injection device 10 may have a different expiry date, dosing time period and/or warm-up time period stored in the device tag.

It will be appreciated that the above described embodiments are purely illustrative and are not limiting on the scope of the claims. Other variations and modifications will be apparent to persons skilled in the art upon reading the present application, and some will now be described.

The case of the packaging arrangement may be a generally rectangular shape or may be any other shape suitable for containing the plurality of injection devices. The case may be a suitable shape and size for placement within a household refrigerator.

The case may be configured to store any number of injection devices, according to the dosage requirements of the medicament. For example, the case may store between 5 and 15 injection devices. Case may be sized to store enough injection devices for one quarter, or for a 6 month period. Where medicament is administered more regularly, the case may store enough injection devices for one week.

The case may be formed of an opaque material. One or more of the components of the case may be formed with at least a transparent portion. A transparent portion of the case may allow the user to see the number of injection devices, or to see the user interface. One or more components of the case may be translucent to improve visibility of a visual reminder output.

The case may be formed of a plastics material such as polyethylene, polystyrene, polycarbonate, or it may be made of any other suitable material. Desired properties for the material of the case include temperature stability, moderate impact strength, resistance to cleaning fluids, a wipe-clean finish, and rigidity.

Each part of the case may be formed in a single piece e.g. a molded plastic part. Alternatively, parts may be machined. The body of the case may be formed from two parts joined or attached together, or may be formed in a single part. An interior of the case may be formed as a single large cavity, a cavity divided into a plurality of areas for holding each injection device, or may be formed as a plurality of cavities for individually holding each injection device.

The cooling unit may utilize any active or passive cooling mechanism. For example, the cooling unit may comprise a plurality of cooling packs which are cooled to a low temperature in the refrigerator, and subsequently maintain the low temperature of the case for a period of time.

The lid may be coupled to the case with a hinge. The mechanism for connecting the lid to the case and for allowing the lid to open and close may take any suitable form. Instead of the hinge mechanism described above, the hinge may be a butt hinge, a living hinge or some other type. The lid may be coupled to the case with a flexible and/or elastic material. The hinge may allow some translational movement as well as pure rotational movement, to allow better viewing of or access to the internal part of the case when the lid is open.

The hinge may allow the removal of the lid by a user. The user may be provided with one or more alternative lids which may be a different design, for example, a different color. An alternative lid may have a larger transparent portion or may be entirely opaque.

Alternatively, the lid may slidably engage with the case. The lid may comprise runners at the edges, each configured to engage with a corresponding groove on the case. The lid may slide out of the grooves and decouple from the case.

The lid may be arranged to slide to the limit of the grooves and pivot freely in the open position. Further alternatively, the lid may be separate from the case and fixedly attached thereto with a friction fit. The lid may fit tightly within the opening at the upper end of the case, or may fit over an upper portion of the case.

The electronic system may include a lid open sensor, such as an electromechanical switch. The lid open sensor may provide the processor arrangement with a signal indicating whether the lid of the case is open or closed. The lid open sensor may instead be an optical sensor arrangement, a magnetic sensor arrangement or any other suitable arrangement that is configured to detect whether the lid is open or closed or whether the lid is transitioning from a closed position to an open position.

The processor arrangement may record the status of the lid on the removable storage. In addition, the lid being moved from a closed position to an open position may indicate a user action e.g. to deactivate the audio reminder alert.

Alternative device sensor may include optical sensors. Optical device tags such as, for example, barcodes or QR codes, may be provided on the plurality of injection devices. Alternatively, optical sensors may determine a color or visual marking on an injection device to determine the type of injection device. In some embodiments, an optical sensor detects the presence of an injection device without receiving further device information. A device sensor may be implemented with a mechanical switch arranged to be pressed by an injection device when placed in the slot. The processor arrangement may determine the number of injection devices, the location of the injection devices and generate a device index for each injection device based on the detected presence of the injection devices. An alternative processor arrangement may iterate the device index only if both the device type and expiry date of an injection device match those of another injection device.

The device sensor may comprise one or more device switches. The device switches may be arranged respectively within the openings. Each device switch may be a mechanical switch. The device switch may be a normally open switch which is pressed to a closed position by an injection device when in position in the opening. The device switch may be a membrane switch. The device switch may be actuated by a lever located within the opening.

Each device switch may be configured to send a signal to the processor arrangement when an injection device is located within the corresponding slot. The processor arrangement may be configured to activate or deactivate the speaker when a signal is no longer received from a device switch. The processor arrangement may be configured further to reset the countdown to the scheduled dosing time when an injection device is removed from the slot. Alternatively, where an injection device is replaced in the case after the dose is administered, the processor arrangement may be configured to reset the countdown when the injection device is replaced. The processor arrangement may be configured to monitor the number of injection devices in position in the packaging assembly. The processor arrangement may control the display to show the number of injection devices in the packaging assembly. The processor arrangement may control the electronics system to provide a notification output when the packaging assembly is empty.

In some embodiments, the add-on device may include an RFID sensor. The functionality of the device sensor of the electronics system may be performed by a device sensor in the add-on device. Signals from the device sensor in the add-on device may be transmitted to the processor arrangement.

In some embodiments, the communication unit of the add-on device may communicate with the processor arrangement through the docking connector only. Injection information for the injection device may be transmitted to the add-on device through the wired connection before the injection device is removed from the case. Data to be transmitted to the processor arrangement may be stored on the add-on device and downloaded when the add-on device is returned to the case.

The time period for a reminder may be any suitable dosing period, dependent upon the medicament which is stored in the packaging assembly. The time period set until the next scheduled dosing time may be any number of days and may be, for example, between 2 and 60 days. The time period may be a number of weeks, for example, a period of 7 days, 14 days, 21 days or 28 days. The time period may be 28 days, which is 4 weeks, or the time period may be 1 month. A different time period might be applied upon selecting the countdown timer duration, based on the current weekday or the exact date within the month or the year. A different time period may be set for each injection device. The time period for an injection device may be recorded on the injection device and may be read by the device sensor. The time period for a type of injection device may be stored in the non-volatile memory.

A time period may be fixed for all injection devices. A predetermined time period may be stored in the non-volatile memory. Alternatively, a timer duration switch may be configured to select between any two time periods. For example, a first switch position may correspond to a time period of 7 days and a second switch position may correspond to a time period of 14 days. Alternatively, the timer duration switch may be a multi-positional switch, for example, a rotary switch or a dial. The time period may be set in conjunction with a display, wherein a first user input causes the display to show the current time period, and a second input is used to adjust the time period. A third input might be used to confirm the new settings.

An external display may comprise more than 2 LED arrays, to accommodate larger numbers and messages, or more be a single LED array only. In any embodiment, the external display or the internal display may include any form of electronic display suitable for displaying a number and/or a message, for example, the display may be an array of LED pixels, an LCD or e-paper screen, or a split-flap display. The display may be a display which is capable of displaying pseudo-3D images or video, e.g. a lenticular display. The display may be arranged in a peripheral module which is separate from the case. The display module may be connected to electrics system with a wired or wireless connection. The electronics system may comprise any display driver which is suitable for the chosen display.

The display may be configured to provide further status information, or more detail, in the form of text messages on the display. For example, the display may provide a visual reminder that the scheduled dosing time is due by showing a reminder message. The display may be controlled to show the number of injection devices remaining in the packaging assembly. The processor arrangement may be configured to determine the number of injection devices according to an input from the sensor array. Alternatively, the processor arrangement may be configured to monitor the number of times that a scheduled dosing time has passed. The display may be controlled to show a notification message when the packaging assembly is empty.

The display might be used to display a short sequence of pictures or a video, in 2D or in 3D, to show the correct usage or application of the injection device. The display may show any other useful information or advice connected to the therapy or the daily life of the patient.

The speaker may be any suitable form of audio output transducer, for example, an electro-acoustic transducer, a piezoelectric buzzer, a moving diaphragm speaker, or a mechanical bell. A vibrating alert may be used instead of or in addition to the audio output transducer. The speaker may output a different alert output, according to the type of device. For example, the speaker may vary the periodicity of an intermittent tone, or the frequency of the tone, or may output a pre-defined tone sequence e.g. a 3-tone sequence. Alternatively, the speaker may be configured to reproduce a digital audio file stored in the non-volatile memory. The reproduced digital audio file may be up to 6 seconds long or, alternatively, may be longer than 6 seconds.

A unique or individual alert may be used for each device type or, for example, to distinguish between alerts for different users of the packaging assembly. Audio alerts may be customizable by the user. In addition to an audio alert, the audio output of the speaker may be used to improve usability in other ways. For example, an audio output may indicate when an injection device is detected by the sensor array. A different audio output may be used according to whether the injection device is being inserted or removed.

Alternative countdown timer implementations include off-chip and on-chip state-based logic circuits with clock devices, and other forms will be apparent to the skilled person.

The PCB and components of the electronics system may be sealed for protection. For example, the PCB may be coated on each side with a water resistant lacquer or another suitable coating. The electronics system may be coated for protection from moisture or humidity in the interior of a household fridge.

In some embodiments, the removable storage may be a further non-volatile storage medium which cannot be removed from the electronics system. The removable storage may be part of the non-volatile memory. The user may access a non-removable storage of this type via the wireless communication module, as described above.

The packaging assembly may include a greater or smaller number of batteries, according to the power requirements of the electronics system. For example, the packaging assembly may include a single battery power pack. The battery or batteries may be removable and replaceable, or may be fixed within the case of the packaging assembly. Alternatively, the packaging assembly may be adapted for a mains power supply, or any alternative power supply.

The term "device type" is used to describe the physical sum of a drug container with a given drug and a given drug concentration, and the mechanical/electronic object performing relevant steps of the drug injection into the patient. The device type may be represented by one field in the device table or alternatively, for example, by two or more dependent fields to define the device type e.g. by specifying any of the medicament, concentration and delivery method of the injection device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary). The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about –4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalentantibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A case comprising:
an opening configured to receive a plurality of injection devices;
a cooling unit configured to adjust an environmental condition of the case while the plurality of injection devices are in the case; and
a wireless communication module configured at least to transmit first information to a monitoring device of an injection device of the plurality of injection devices, the monitoring device configured to be releasably attached to the injection device,
wherein the wireless communication module is further configured to transmit a warm-up time period to an external user device, the warm-up time period representing the recommended period of time to wait before injection to allow the injection device to reach room temperature.

2. The case of claim 1, further comprising a device sensor configured to receive second information of the injection device.

3. The case of claim 2, wherein the second information comprises information of a medicament of the injection device, an identifier of the injection device, or a warm-up time of the injection device.

4. The case of claim 3, further comprising a display; and wherein the one or more processors are further configured to control the display of the case to show at least the first information.

5. The case of claim 4, further comprising a lid configured to move between an open position and a closed position, wherein the display of the case is obscured when the lid is in the closed position, and wherein the display of the case is uncovered when the lid is in the open position.

6. The case of claim 1, wherein the first information comprises an instruction of using the injection device to the monitoring device.

7. The case of claim 6, wherein the case is configured to receive a status of the injection device from the monitoring device.

8. The case of claim 7, further comprising a data storage device configured to record the status of the injection device.

9. The case of claim 8, wherein the data storage device comprises a removable, computer readable storage medium.

10. The case of claim 8, further comprising one or more processors configured to (i) record the status of the injection device on the data storage device, (ii) control the cooling unit to adjust an environmental condition of the case, and (iii) control the wireless communication module to transmit the first information to the monitoring device.

11. The case of claim 1, further comprising a docking connector configured to engage with the monitoring device for charging a battery of the monitoring device.

12. The case of claim 1, wherein the environmental condition is at least one of a temperature or a humidity.

13. The case of claim 1, wherein the wireless communication module is configured for two-way communication with the monitoring device.

\* \* \* \* \*